United States Patent
Ogawa

(10) Patent No.: US 9,168,570 B2
(45) Date of Patent: Oct. 27, 2015

(54) CLEANING PROCESSING DEVICE FOR BIOLOGICAL IMPLANT

(75) Inventor: Yoshimasa Ogawa, Himeji (JP)

(73) Assignee: USHIO DENKI KABUSHIKI KAISHA, Tokyo (JP)

( * ) Notice: Subject to any disclaimer, the term of this patent is extended or adjusted under 35 U.S.C. 154(b) by 203 days.

(21) Appl. No.: 13/823,397

(22) PCT Filed: Sep. 5, 2011

(86) PCT No.: PCT/JP2011/070163
§ 371 (c)(1),
(2), (4) Date: Mar. 14, 2013

(87) PCT Pub. No.: WO2012/043157
PCT Pub. Date: Apr. 5, 2012

(65) Prior Publication Data
US 2013/0167873 A1    Jul. 4, 2013

(30) Foreign Application Priority Data
Sep. 30, 2010 (JP) ................................. 2010-221828

(51) Int. Cl.
*B08B 7/00* (2006.01)
*A61L 2/10* (2006.01)
(Continued)

(52) U.S. Cl.
CPC ............. *B08B 7/0057* (2013.01); *A61L 2/10* (2013.01); *A61C 8/00* (2013.01); *A61C 19/002* (2013.01); *A61L 2202/11* (2013.01); *A61L 2202/21* (2013.01)

(58) Field of Classification Search
CPC .... A61C 19/002; A61L 2202/11; A61L 2/10; A61L 2/202; B08B 7/0057

USPC ............................ 134/18, 56 R, 104.2, 105
See application file for complete search history.

(56) References Cited

U.S. PATENT DOCUMENTS 4,772,795 A * 9/1988 Sakurai .................. A61L 2/10
250/455.11
5,185,532 A * 2/1993 Zabsky .................. A61L 2/10
250/455.11
(Continued)

FOREIGN PATENT DOCUMENTS

JP           06-081682 U     11/1994
JP           2000-066003 A   3/2000
(Continued)

*Primary Examiner* — Michael Kornakov
*Assistant Examiner* — Katelyn Whatley
(74) *Attorney, Agent, or Firm* — Fitzpatrick, Cella, Harper & Scinto

(57) ABSTRACT

Provided is a cleaning processing device that is for a biological implant and that is capable of quickly eliminating ozone generated by ultraviolet-ray radiation after completion of ultraviolet-ray radiation towards the biological implant. The cleaning processing device for a biological implant performs cleaning processing of the biological implant by means of radiating ultraviolet rays at the surface of the biological implant and by causing ozone to contact the surface of the biological implant, and the cleaning processing device is characterized by being provided with a housing, an ultraviolet-ray radiating lamp that is disposed within the housing and that radiates ultraviolet rays at the biological implant, an ozone-removing filter disposed within the housing, and a fan that introduces the ambient gas within the housing to the ozone-removing filter, and is further characterized by the fan being driven in response to the end of cleaning processing of the biological implant.

7 Claims, 6 Drawing Sheets

(51) Int. Cl.
*A61C 8/00* (2006.01)
*A61C 19/00* (2006.01)

(56) References Cited

U.S. PATENT DOCUMENTS

| | | | |
|---|---|---|---|
| 6,402,517 B1 | 6/2002 | Hozumi et al. | 433/201.1 |
| 6,605,260 B1* | 8/2003 | Busted | A61L 2/10 |
| | | | 426/248 |
| 2004/0156959 A1* | 8/2004 | Fink | A23L 3/36 |
| | | | 426/248 |

| | | | | | |
|---|---|---|---|---|---|
| 2013/0264495 A1* | 10/2013 | Ogawa | | | A61L 2/0047 |
| | | | | | 250/455.11 |

FOREIGN PATENT DOCUMENTS

| | | | | |
|---|---|---|---|---|
| JP | 2000066003 A * | 3/2000 | | G02B 1/10 |
| JP | 2001-017447 A | 1/2001 | | |
| JP | 2005-080808 A | 3/2005 | | |
| JP | 2005-342314 A | 12/2005 | | |
| JP | 2005342314 A * | 12/2005 | | A61L 2/20 |
| JP | 2010-068875 A | 4/2010 | | |

\* cited by examiner

CLEANING PROCESSING DEVICE FOR BIOLOGICAL IMPLANT

CROSS REFERENCE TO RELATED APPLICATIONS

The present application is a national-stage entry of International Application No. PCT/JP2011/070163 filed on Sep. 5, 2011, and claims the benefit of priority of Japanese Application No. 2010-221828 filed on Sep. 30, 2010.

TECHNICAL FIELD

The present invention relates to a cleaning processing device for a biological implant, which performs a cleaning operation by radiating ultraviolet rays to a biological implant, and causing ozone to make contact with the biological implant.

BACKGROUND ART

Dental implants are implanted into the jawbone so as to substitute for lost teeth. Further, in a dental implant surgery, it is important for a dental implant to be sufficiently coupled to the bone (osseointegration). To this end, it has been proposed to remove organic matter from a dental implant by radiating ultraviolet rays onto the dental implant (see, patent document 1).

On the other hand, in a cleaning processing device used for UV cleaning operation, if oxygen is present in the atmospheric gas within a processing chamber in which a subject to be processed (hereinafter, simply referred to as "a subject") is disposed, radiated ultraviolet rays result in the generation of ozone. Thereby, the subject is subjected to both the ultraviolet-ray radiation and the ozone treatment, so that the organic matter can be very efficiently removed from the subject due to a synergy effect resulting from the ultraviolet-ray radiation and the ozone treatment.

Moreover, the cleaning process using the ultraviolet rays and the ozone is considered to be capable of very efficiently eliminating organic matter from a biological implant other than a dental implant, for example, a femur implant or the like.

CITATION LIST

Patent Literature (Patent Document 1) Japanese Patent Publication No. 3072373

DISCLOSURE

Technical Problem

Further, in order to prevent organic matter from being re-attached to a biological implant in biological implant surgery, including dental implant surgery, it is important to rapidly surgically implant the biological implant after the ultraviolet-ray radiation to the biological implant has been completed.

However, immediately after the cleaning process for the biological implant has been completed, ozone harmful to the human body is contained in the atmospheric gas within the processing chamber in which a biological implant is disposed, so that it is substantially difficult to rapidly take the biological implant out of the processing chamber and then surgically implant the biological implant.

Further, in order to prevent ozone from being generated, a purging means has been proposed which uses inert gas, such as nitrogen gas, for purging the processing chamber in which the biological implant is disposed. However, since such a means does not perform the ozone treatment on the subject, it is difficult to very efficiently remove organic matter from the biological implant.

Accordingly, the present invention has been made keeping in mind the above problems occurring in the prior art, and an object of the present invention is to provide a cleaning processing device for a biological implant, capable of rapidly eliminating ozone used for a cleaning process, after the cleaning process for the biological implant has been completed.

Technical Solution

In order to accomplish the above object, the present invention provides a cleaning processing device for a biological implant, intended to clean the biological implant by radiating ultraviolet rays to a surface of the biological implant and also causing ozone to come into contact with the surface thereof, the device including a housing, an ultraviolet-ray radiating lamp disposed in the housing to radiate the ultraviolet rays to the biological implant, an ozone-removing filter disposed in the housing, and a fan introducing atmospheric gas present in the housing into the ozone-removing filter, wherein the fan is driven in response to completion of a cleaning process for the biological implant.

Preferably, the housing may include a processing chamber for cleaning the biological implant, and an ozone-removing chamber for removing the ozone from the processing chamber, the ultraviolet-ray radiating lamp may be disposed in the processing chamber, the fan may be disposed in the ozone-removing chamber, the ozone-removing filter may be disposed on a flow path that is formed by the fan in the ozone processing chamber, and the atmospheric gas present in the processing chamber may be circulated through the ozone processing chamber, by driving the fan.

Preferably, in such a cleaning processing device for the biological implant, a partition wall may be provided to partition the processing chamber from the ozone-removing chamber, at least one of the housing and the partition wall may be made of metal, and heat caused by light from the ultraviolet-ray radiating lamp may be transferred through the housing or the partition wall made of the metal to the ozone-removing filter.

Further, a reflecting mirror made of metal may be disposed in the processing chamber to reflect light from the ultraviolet-ray radiating lamp, and the heat caused by the light from the ultraviolet-ray radiating lamp may be transferred through the reflecting mirror to the ozone-removing filter.

Furthermore, ozone-removing filters may be provided on the flow path formed by the fan in such a way as to be located on both an upstream side and a downstream side of the fan, with a closed space defined between the ozone-removing filters.

In the cleaning processing device for the biological implant according to the present invention, the housing may include a discharge hole to discharge the atmospheric gas from the housing to an outside, and the fan may be disposed in the discharge hole, the ozone-removing filter being disposed to face the fan.

Advantageous Effects

As described above, the present invention provides a cleaning processing device for a biological implant, which introduces atmospheric gas, present in a housing in which the biological implant is disposed, into an ozone-removing filter by driving a fan as a cleaning process is completed, and thus removes ozone from the atmospheric gas, a result of which is that the ozone contained in the atmospheric gas within the housing can be rapidly removed after the cleaning process for the biological implant has been completed.

MODE FOR INVENTION

Figure 1:
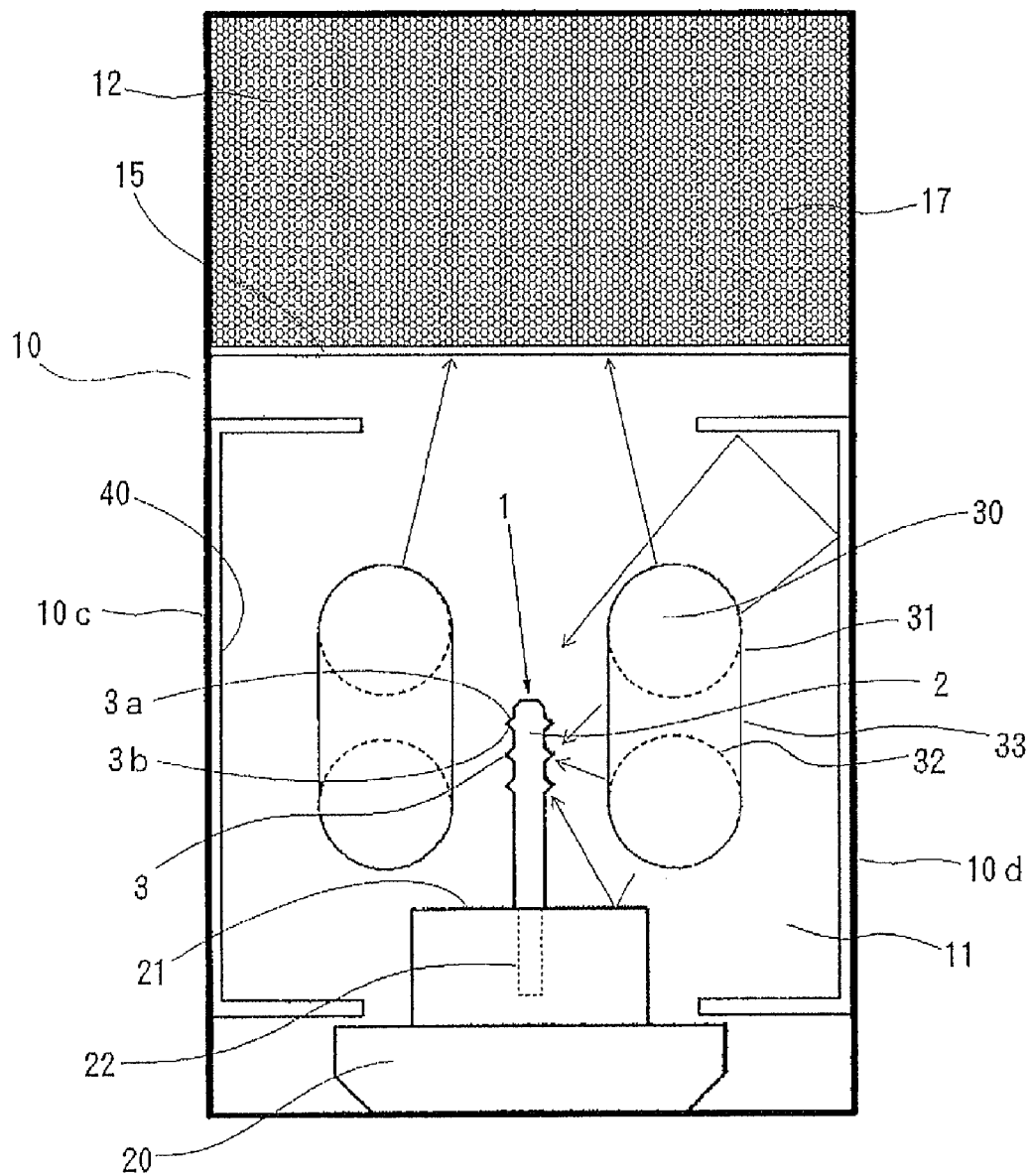
FIG. 1 is a front view illustrating an internal configuration of a housing of a cleaning processing device for a biological implant according to an embodiment of the present invention.
Figure 2:
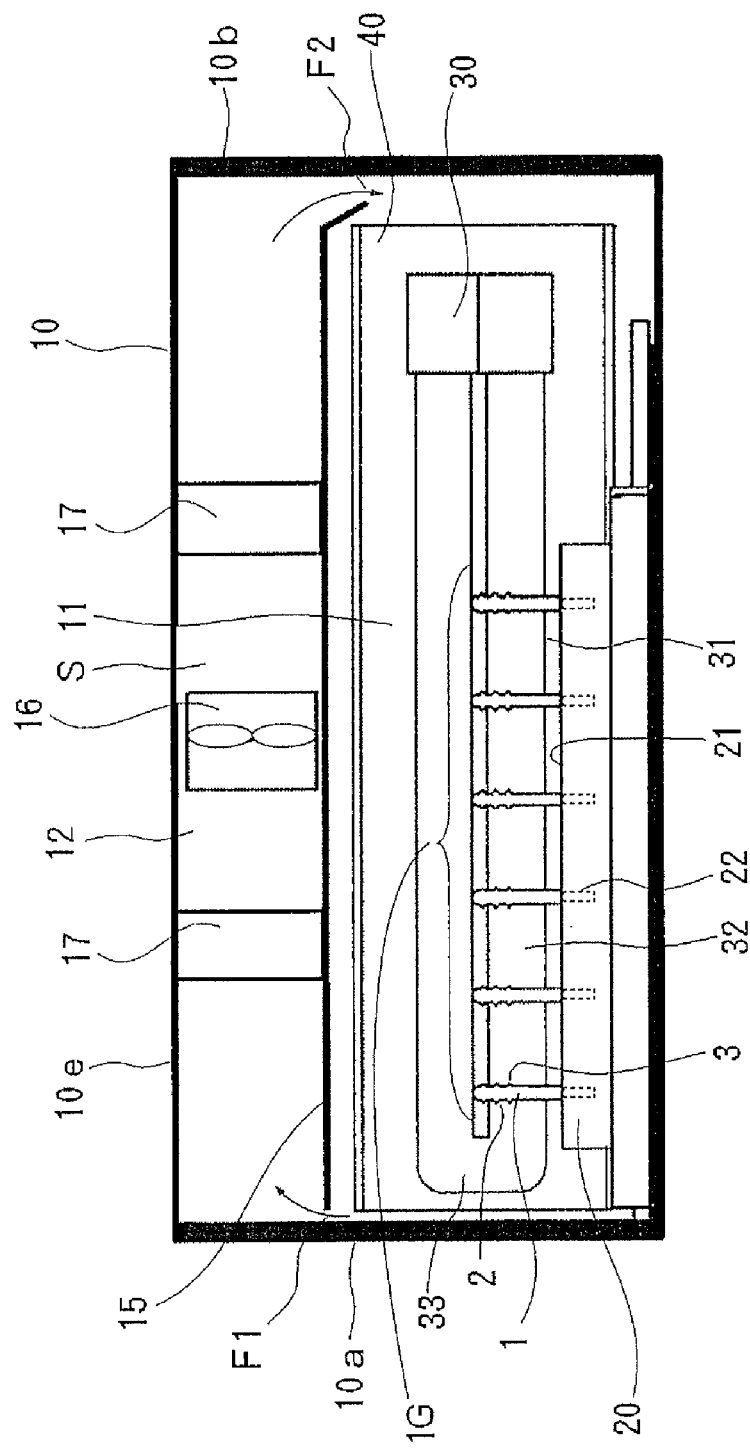
FIG. 2 is a side view illustrating the internal configuration of the housing of the cleaning processing device for the biological implant according to an embodiment of the present invention.
Figure 3:
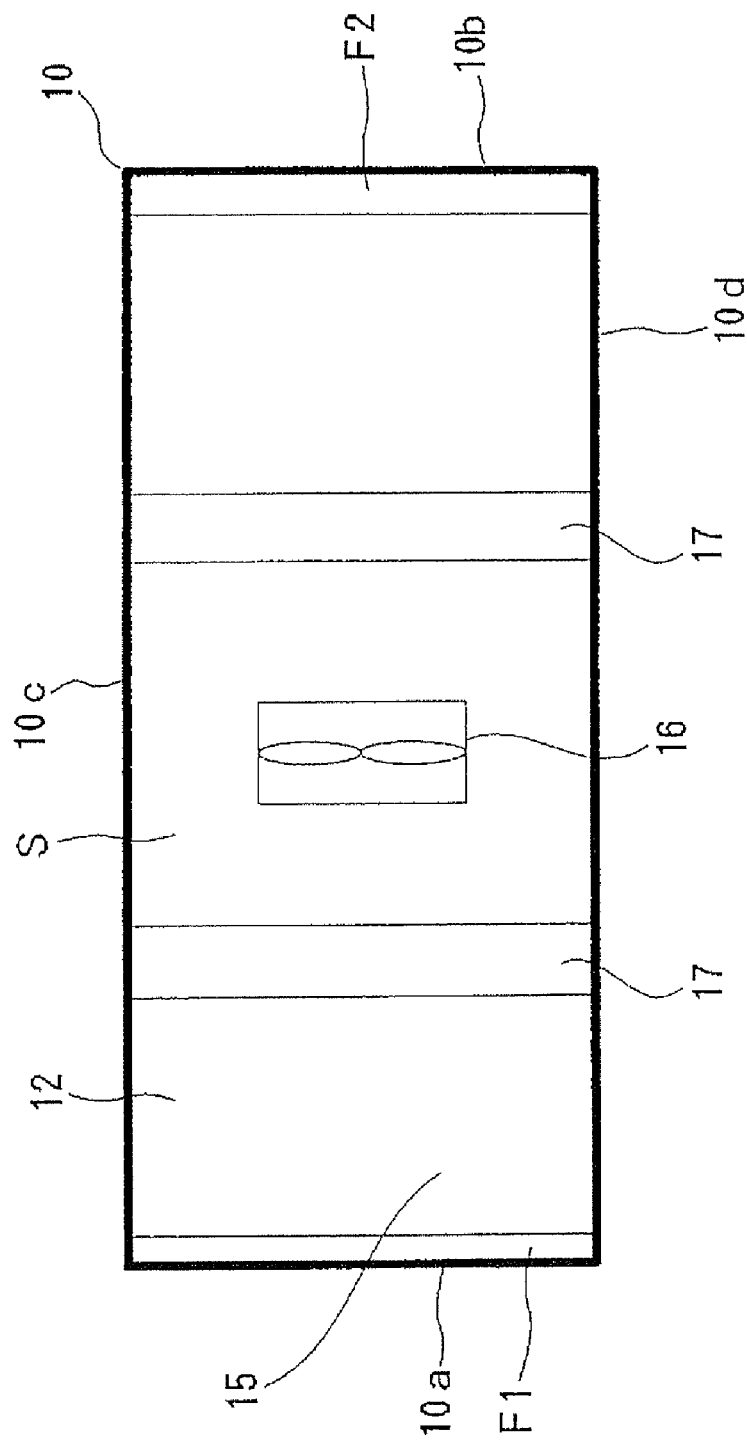
FIG. 3 is a plan view illustrating an ozone-removing chamber of the cleaning processing device for the biological implant according to an embodiment of the present invention.

FIG. 1 is a front view illustrating an internal configuration of a housing of a cleaning processing device for a biological implant according to an embodiment of the present invention, FIG. 2 is a side view illustrating the internal configuration of the housing of the cleaning processing device for the biological implant according to an embodiment of the present invention, and FIG. 3 is a plan view illustrating an ozone-removing chamber of the cleaning processing device for the biological implant according to an embodiment of the present invention.

The cleaning processing device for the biological implant (hereinafter, simply referred to as a (cleaning processing device)) is intended to clean an implant 1 by radiating ultraviolet rays to a pin-shaped dental implant 1 (hereinafter, simply referred to as an (implant)) and also causing ozone to make contact with the dental implant. In the illustrated embodiment, the implant 1 is a screw type having a threaded portion 2 which has on an end thereof a protrusion 3 in a spiral form.

The cleaning processing device includes a housing 10 that has an entire contour of a rectangular shape, with a door (not shown) provided on a front of the housing. In this housing 10 is provided a processing chamber 11 in which a plurality of implants 1 is disposed. Moreover, above the processing chamber 11 is provided an ozone-removing chamber 12 to remove ozone from the atmospheric gas in the processing chamber 11. The processing chamber 11 and the ozone-removing chamber 12 are partitioned from each other by a partition wall 15. This partition wall 15 is spaced apart from a front sidewall 10a and a rear sidewall 10b of the housing 10, respectively, so that an inlet F1 is defined between the front sidewall 10a of the housing 10 and the partition wall 15 to allow gas to flow from the processing chamber 11 to the ozone-removing chamber 12, and an outlet F2 is defined between the rear sidewall 10b of the housing 10 and the partition wall 15 to allow gas to be discharged from the ozone-removing chamber 12 to the processing chamber 11.

In the processing chamber 11 of the housing 10 is installed a stage 20 on which a plurality of implants 1 is arranged and held to be aligned in one direction (a direction perpendicular to the ground in FIG. 1, a horizontal direction from left to right in FIG. 2). More specifically, a plurality of holding portions 22 is provided on a surface 21 of the stage 20 in such a way as to be aligned in one direction, each holding portion comprising a concave portion with an inner diameter corresponding to an outer diameter of the other end of each implant 1. The other end of the implant 1 is inserted and held in each holding portion 22 while being erected in such a way that an end of the threaded portion 2 of the implant 1 faces upwards, so that a plurality of implants 1 is aligned in one direction.

Further, in the illustrated embodiment, the surface of the stage 20 undergoes a mirror surface finishing, for example, so that this surface becomes a light reflecting surface that reflects ultraviolet rays from an ultraviolet-ray radiating lamp 30 that will be described later.

Further, the stage 20 may be removably installed in the housing 10. Such a configuration enables the stage 20 to be taken out of the housing 10, thus making it easy to perform an attaching, removing, or replacing operation of the implant 1 with respect to the stage 20.

In an implant group 1G consisting of the plurality of implants 1 that are held in the stage 20, two ultraviolet-ray radiating lamps 30 are provided on both sides parallel to one direction in which the implants 1 are aligned. In a detailed description, each ultraviolet-ray radiating lamp 30 has a light emitting pipe 31 in the form of a U-shaped pipe wherein two linear portions 32 extending in one direction in which the respective implants 1 are aligned are connected to each other by a curved portion 33. The two ultraviolet-ray radiating lamps 30 are placed to face each other, via the threaded portion 2 of the implant 1 and the surrounding spatial region thereof, in such a way that the two linear portions 32 of each light emitting pipe 31 are located one above the other. Further, two reflecting mirrors 40 having a section of a U-shaped recess are provided between each ultraviolet-ray radiating lamp 30 and a sidewall 10c or 10d of the housing 10 to reflect ultraviolet rays from the ultraviolet-ray radiating lamp 30, and are placed to face the ultraviolet-ray radiating lamps 30 in such a way that rear surfaces thereof are in contact with the sidewalls 10c and 10d of the housing 10.

In the illustrated embodiment, the housing 10, the partition wall 15 and the stage 20 are respectively made of a metal such as stainless steel, and the reflecting mirror 40 is made of a metal such as aluminum.

As the ultraviolet-ray radiating lamp 30, it is possible to use a low-pressure mercury lamp that emits a ultraviolet ray having a wavelength of 254 nm and a ultraviolet my having a wavelength of 185 nm. Further, the illumination intensity of ultraviolet rays from the ultraviolet-ray radiating lamp 30 is about 6 mW/cm$^2$ or higher, at a position spaced apart by 10 mm from a wall of the light emitting pipe 31.

An example of the low-pressure mercury lamp used as the ultraviolet-ray radiating lamp 30 has the following specification: the light emitting pipe is made of synthetic quartz glass, a light emitting length is 200 mm, and a lamp input is 25 W.

A fan 16 is disposed in the ozone-removing chamber 12 of the housing 10 to circulate atmospheric gas in the processing chamber 11 through the ozone-removing chamber 12. Further, ozone-removing filters 17 each having a shape of a rectangular plate are disposed, respectively, on the upstream side and the downstream side of the fan 16 in a circulating flow path defined by the fan 16. Each ozone-removing filter 17 is fixedly press-fitted into the ozone-removing chamber 12 in the state where four side surfaces of the filter come into contact with the sidewalls 10c and 10d and an upper wall 10e of the housing 10 and the partition wall 15, so that a closed space S is formed between the two ozone-removing filters 17.

The ozone-removing filter 17 is made such that an ozone-removing catalyst made of a manganese compound, for example, is supported in a substrate having a honeycomb structure made of inorganic fiber paper, for example.

In such a cleaning processing device, the implant is erected and held in each holding portion 22 of the stage 20 in such a way that the end of the threaded portion 2 of the implant 1 faces upwards. In such a state, by turning each ultraviolet-ray radiating lamp 30 on, the ultraviolet rays are directly radiated from the ultraviolet-ray radiating lamp 30 to the protrusion 3 forming the threaded portion 2 of the implant 1, and besides are reflected from the reflecting mirror 40 and the surface of the stage 20, respectively. Consequently, the ultraviolet rays are radiated to the entire surface of the protrusion 3, and also the ultraviolet rays are radiated from the ultraviolet-ray radiating lamp 30 to the oxygen in the atmospheric gas present in the processing chamber 11, so that the ozone is generated in the processing chamber 11 and is in contact with the threaded portion 2 of the implant 1. As such, the ultraviolet rays are radiated to the entire surface of the protrusion 3 forming the threaded portion 2 of the implant 1, namely, both an upper surface 3a and a lower surface 3b of the protrusion 3, and also the ozone comes into contact with the threaded portion 2, so that organic matter attached to the threaded portion 2 of the implant 1 is decomposed and removed, and thereby the cleaning process for the implant 1 is achieved.

On the other hand, the partition wall 15 and the reflecting mirror 40 are heated, respectively, by radiating light from the ultraviolet-ray radiating lamp 30. Since the partition wall 15 is made of metal, heat generated from the partition wall 15 is transferred to the ozone-removing filter 17. Further, since each of the reflecting mirror 40 and the housing 10 is made of metal, heat generated from the reflecting mirror 40 is transferred through the housing 10 to the ozone-removing filter 17, and thereby the ozone-removing filter 17 is heated.

Further, by turning the ultraviolet-ray radiating lamp 30 off, the cleaning process for the implant 1 is completed. As the cleaning process has been completed, the fan 16 is driven, so that the atmospheric gas in the processing chamber 11 is circulated through the ozone-removing filter 17 disposed in the ozone-removing chamber 12. As a result, the ozone generated in the processing chamber 11 is removed, and then the implant 1 is taken out of the processing chamber 11.

In the above, the ultraviolet-ray radiating time from the ultraviolet-ray radiating lamp 30 is, for example, 5 to 30 minutes.

Further, the concentration of the ozone generated in the processing chamber 11 by the ultraviolet-ray radiation is preferably 100 ppm or more, more preferably 200 to 400 ppm.

In addition, the fan 16 is driven when the cleaning process for the implant 1 is completed (in the illustrated embodiment, when the ultraviolet-ray radiating lamp 30 is turned off). The timing of driving the fan 16 may be at the same time as the cleaning process for the implant 1 is completed, or may be before or after the cleaning process for the implant 1 is completed.

Furthermore, the operating time of the fan 16, namely, the ozone removing time is appropriately set in consideration of the ozone removing capability of the ozone-removing filter 17, for example, 10 to 300 seconds.

Moreover, when the ozone removing operation is completed in the processing chamber 11, the concentration of the ozone is preferably 0.1 ppm or less.

Further, the ozone-removing filter 17 is heated by transferring heat, caused by light from the ultraviolet-ray radiating lamp 30, through the partition wall 15, the reflecting mirror 40 and the housing 10. The temperature of the ozone-removing filter 17 is 50 to 60° C. when the ultraviolet-ray radiating lamp 30 is turned off, for example.

In the above cleaning processing device, the fan 16 is driven in response to the completion of the cleaning process, so that the atmospheric gas in the processing chamber 11 in which the implant 1 is disposed is circulated through the ozone-removing filter 17 in the ozone-removing chamber 12, and thereby the ozone is removed from the atmospheric gas. Hence, after the cleaning process for the biological implant 1 is completed, the ozone can be rapidly removed from the atmospheric gas in the processing chamber 11.

Further, since the ozone-removing filter 17 is heated by transferring heat caused by light from the ultraviolet-ray radiating lamp 30 through the partition wall 15, the reflecting mirror 40 and the housing 10, the activity of the catalyst for removing the ozone of the ozone-removing filter 17 is increased, and consequently it is possible to very efficiently perform the ozone removing operation.

Furthermore, the ozone-removing filters 17 are located on both the upstream side and the downstream side of the fan 16 on the circulating flow path formed by the fan 16, and the closed space S is formed in the two ozone-removing filters 17, thus preventing gas containing ozone of high concentration from coming into contact with the fan 16, and thereby preventing parts of the fan 16 from being corroded by the ozone even if some parts of the fan 16 are made of a material that is apt to corrode by the ozone, for example, a resin material.

Figure 4:
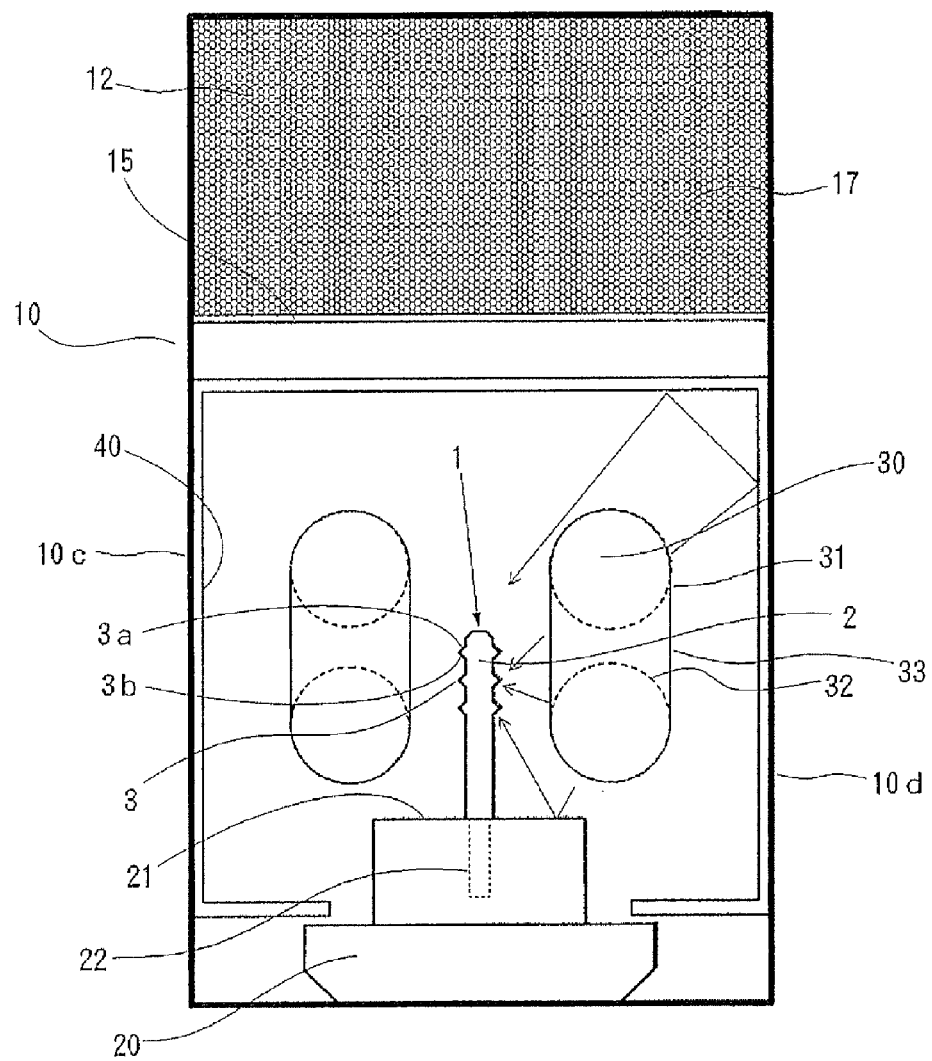
FIG. 4 is a front view illustrating an internal configuration of a housing of a cleaning processing device for a biological implant according to another embodiment of the present invention.
Figure 5:
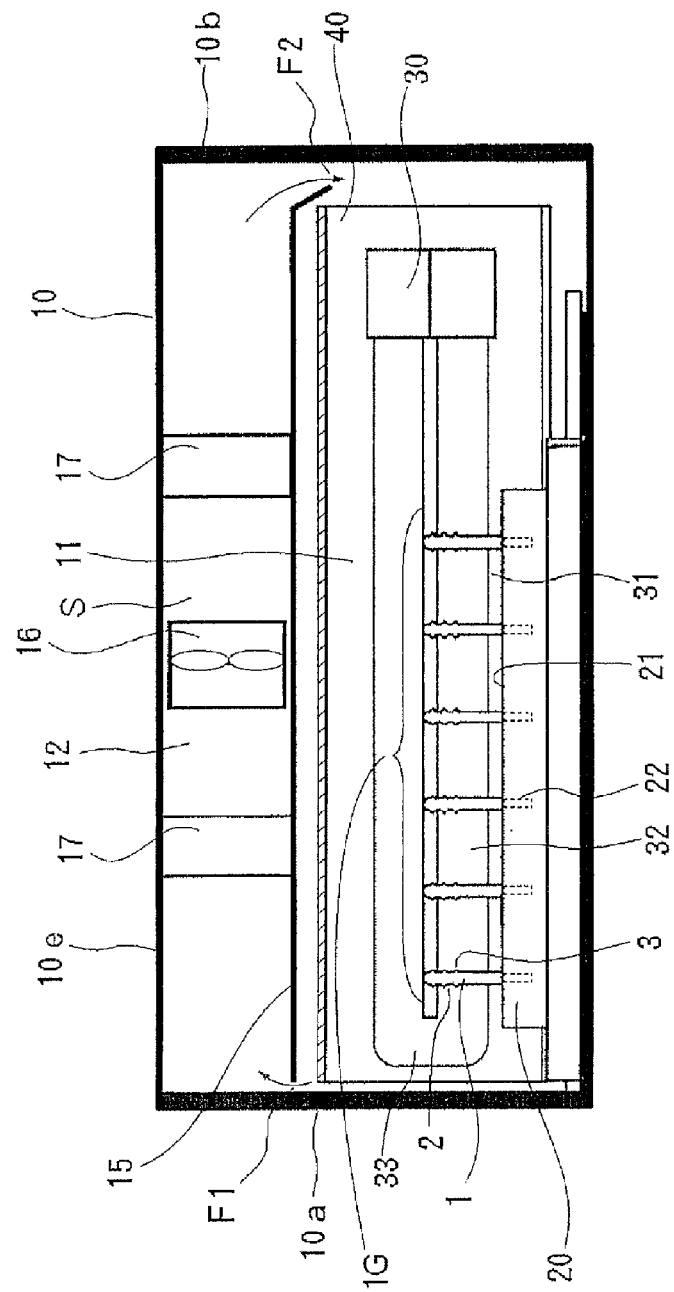
FIG. 5 is a side view illustrating the internal configuration of the housing of the cleaning processing device for the biological implant according to another embodiment of the present invention.

FIG. 4 is a front view illustrating an internal configuration of a housing of a cleaning processing device for a biological implant according to another embodiment of the present invention, and FIG. 5 is a side view illustrating the internal configuration of the housing of the cleaning processing device for the biological implant according to another embodiment of the present invention.

In this cleaning processing device, in the state where the reflecting mirror 40 of a rectangular box shape, which has on one surface thereof an opening for receiving the stage 20 and reflects ultraviolet rays from the ultraviolet-ray radiating lamp 30, contacts on a side surface thereof the sidewalls 10c and 10d of the housing 10, and is spaced at an upper surface thereof apart from the partition wall 15, the reflecting mirror is disposed to surround the stage 20, the implant group G1 comprising the plurality of implants 1 held in the stage 20, and the ultraviolet-ray radiating lamp 30. The remaining configuration remains the same as the cleaning processing device shown in FIGS. 1 to 3.

In such a cleaning processing device, the implant 1 is erected and held in each holding portion 22 of the stage 20 in such a way that the end of the threaded portion 2 thereof faces upwards. In this state, by turning each ultraviolet-ray radiating lamp 30 on, the ultraviolet-ray radiating lamp 30 radiates ultraviolet rays to the protrusion 3 forming the threaded portion 2 of the implant 1, and besides the ultraviolet rays are reflected from the reflecting mirror 40 and the surface of the stage 20. Consequently, the ultraviolet rays are radiated to the entire surface of the protrusion 3, and besides the ultraviolet-ray radiating lamp 30 radiates ultraviolet rays to the oxygen in the atmospheric gas within the processing chamber 11, so that ozone is generated in the processing chamber 11 and is in contact with the threaded portion 2 of the implant 1. As such, the ultraviolet rays are radiated to the entire surface of the protrusion 3 forming the threaded portion 2 of the implant 1, namely, both the upper surface 3a and the lower surface 3b of the protrusion 3, and the ozone comes into contact with the threaded portion 2, so that organic matter attached to the threaded portion 2 of the implant 1 is decomposed and removed, and thereby the cleaning process for the implant 1 is achieved.

On the other hand, the reflecting mirror 40 is heated by radiating light from the ultraviolet-ray radiating lamp 30. Since each of the reflecting mirror 40 and the housing 10 is made of metal, heat generated in the reflecting mirror 40 is transferred through the housing 10 to the ozone-removing filter 17, and thereby the ozone-removing filter 17 is heated.

Moreover, by turning the ultraviolet-ray radiating lamp 30 off, the cleaning process for the implant 1 is completed. In response to the completion of the cleaning process, the fan 16 is driven, so that the atmospheric gas in the processing chamber 11 is circulated through the ozone-removing filter 17 disposed in the ozone-removing chamber 12. As a result, the ozone generated in the processing chamber 11 is removed, and thereafter, the implant 1 is taken out of the processing chamber 11.

In the above, the ultraviolet-ray radiating time from the ultraviolet-ray radiating lamp 30, the concentration of the ozone in the processing chamber 11, the timing when the fan 16 is driven, the operating time of the fan 16, the concentration of the ozone when the ozone in the processing chamber 11 has been removed, and the temperature of the ozone-removing filter 17 remain the same as the cleaning processing device shown in FIGS. 1 to 3.

In the above cleaning processing device, the fan 16 is driven in response to the completion of the cleaning process, so that the atmospheric gas in the processing chamber 11 in which the implant 1 is disposed is circulated through the ozone-removing filter 17 in the ozone-removing chamber 12, and thereby the ozone is removed from the atmospheric gas. Hence, after the cleaning process for the biological implant 1 is completed, the ozone can be rapidly removed from the atmospheric gas in the processing chamber 11.

Further, since the ozone-removing filter 17 is heated by transferring heat caused by light from the ultraviolet-ray radiating lamp 30 through the reflecting mirror 40 and the housing 10, the activity of the catalyst for removing the ozone of the ozone-removing filter 17 is increased, and consequently it is possible to very efficiently perform the ozone removing operation.

Furthermore, the ozone-removing filters 17 are located on both the upstream side and the downstream side of the fan 16 on the circulating flow path formed by the fan 16, and the closed space S is formed in the two ozone-removing filters 17, thus preventing gas containing ozone of high concentration from coming into contact with the fan 16, and thereby preventing parts of the fan 16 from being corroded by the ozone even if some parts of the fan 16 are made of a material that is apt to corrode by the ozone, for example, a resin material.

Figure 6:
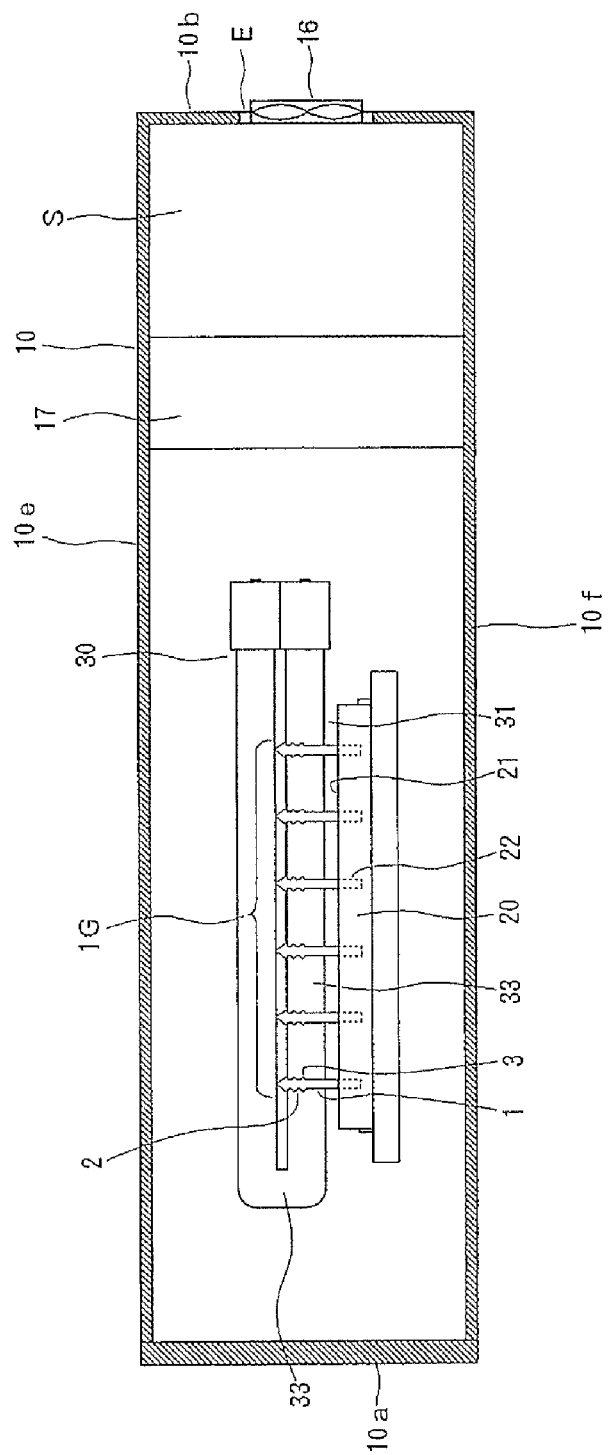
FIG. 6 is a side view illustrating an internal configuration of a housing of a cleaning processing device for a biological implant according to a further embodiment of the present invention.

FIG. 6 is a side view illustrating an internal configuration of a housing of a cleaning processing device for a biological implant according to a further embodiment of the present invention.

The cleaning processing device includes a housing 10 that has an entire contour of a rectangular shape and is made of metal, with a door provided on a front sidewall 10a of the housing. In this housing 10 is installed a stage 20 that has the same configuration as the cleaning processing device of FIG. 1.

In an implant group 1G consisting of the plurality of implants 1 that are held in the stage 20, two ultraviolet-ray radiating lamps 30 having the same configuration as the cleaning processing device of FIG. 1 are provided on both sides parallel to one direction in which the implants 1 are aligned. Here, the two ultraviolet-ray radiating lamps are placed to face each other, via the threaded portion 2 of the implant 1 and the surrounding spatial region thereof, in such a way that the two linear portions 32 of each light emitting pipe 31 are located one above the other.

A discharge hole E is formed in a rear sidewall 10b of the housing 10 to discharge atmospheric gas in the housing 10 to the outside, with a fan 16 located in the discharge hole E. An ozone-removing filter 17 having the same configuration as the cleaning processing device shown in FIG. 1 is disposed to face the fan 16. More specifically, the ozone-removing filter 17 is fixedly press fitted into the housing 10 in the state where four side surfaces thereof are in contact with an upper wall 10e, a lower wall 10f, and two sidewalls of the housing 10, respectively, so that a closed space S is defined between the front sidewall 10b of the housing 10 and the ozone-removing filter 17.

In such a cleaning processing device, the implant is erected and held in each holding portion 22 of the stage 20 in such a way that the end of the threaded portion 2 of the implant 1 faces upwards. In such a state, by turning each ultraviolet-ray radiating lamp 30 on, the ultraviolet rays are radiated from the ultraviolet-ray radiating lamp 30 to the protrusion 3 forming the threaded portion 2 of the implant 1, and also the ultraviolet rays are radiated from the ultraviolet-ray radiating lamp 30 to the oxygen in the atmospheric gas present in the housing 10, so that the ozone is generated in the housing 10 and is in contact with the threaded portion 2 of the implant 1. As such, the ultraviolet rays are radiated to the protrusion 3 forming the threaded portion 2 of the implant 1, and besides the ozone comes into contact with the threaded portion 2, so that organic matter attached to the threaded portion 2 of the implant 1 is decomposed and removed, and thereby the cleaning process for the implant 1 is achieved.

On the other hand, the housing 10 is heated by radiating light from the ultraviolet-ray radiating lamp 30. Since the housing 10 is made of metal, heat generated from the housing 10 is transferred to the ozone-removing filter 17, and besides light emitted from the ultraviolet-ray radiating lamp 30 is radiated to the ozone-removing filter 17, and thereby the ozone-removing filter 17 is heated.

Further, by turning the ultraviolet-ray radiating lamp 30 off, the cleaning process for the implant 1 is completed. As the cleaning process has been completed, the fan 16 is driven, so that the atmospheric gas in the housing 10 is introduced into the ozone-removing filter 17. As a result, the ozone generated in the housing 10 is removed, and then the implant 1 is taken out of the processing chamber 11.

In the above cleaning processing device, the fan 16 is driven in response to the completion of the cleaning process, so that the atmospheric gas in the housing 10 in which the implant 1 is disposed is introduced into the ozone-removing filter 17, and thereby the ozone is removed from the atmospheric gas. Hence, after the cleaning process for the biological implant 1 is completed, the ozone can be rapidly removed from the atmospheric gas in the housing 10.

Further, since the ozone-removing filter 17 is heated by transferring heat caused by light from the ultraviolet-ray radiating lamp 30 through the housing 10 and besides radiating light from the ultraviolet-ray radiating lamp 30, the activity of the catalyst for removing the ozone of the ozone-removing filter 17 is increased, and consequently it is possible to very efficiently perform the ozone removing operation.

Furthermore, the closed space S is formed between the rear sidewall 10b of the housing 10 in which the fan 16 is installed and the ozone-removing filter 17, thus preventing gas containing ozone of high concentration from coming into contact with the fan 16, and thereby preventing parts of the fan 16 from being corroded by the ozone even if some parts of the fan 16 are made of a material that is apt to corrode by the ozone, for example, a resin material.

Although the embodiments of a cleaning processing device according to the present invention have been disclosed for illustrative purpose, various modifications are possible without departing from the scope and spirit of the present invention.

For example, the ultraviolet-ray radiating lamp 30 is not limited to the low-pressure mercury lamp but may use an excimer lamp in which xenon gas is filled, for example, as long as the lamp radiates ultraviolet rays that can generate ozone from oxygen in the air.

Further, the shape and arrangement of the ultraviolet-ray radiating lamp 30 and the reflecting mirror 40 may be appropriately designed without being limited to those shown in FIGS. 1 to 5. For example, the light emitting pipe 31 of the ultraviolet-ray radiating lamp 30 may have the shape of a linear pipe or the entire shape of a rectangle.

Further, in the cleaning processing device according to the above embodiment, the housing 10, the partition wall 15 and the reflecting mirror 40 are respectively made of metal, and heat caused by the light from the ultraviolet-ray radiating lamp 30 is transferred to the ozone-removing filter 17 through the housing 10, the partition wall 15 and the reflecting mirror 40 in the case of the cleaning processing device shown in FIGS. 1 to 3, and is transferred to the ozone-removing filter 17 through the housing 10 and the reflecting mirror 40 in the case of the cleaning processing device shown in FIGS. 4 and 5. However, the heat may be transferred by any one of the housing 10, the partition wall 15 and the reflecting mirror 40. In this case, among the housing 10, the partition wall 15 and the reflecting mirror 40, only the component contributing to the heat transfer to the ozone-removing filter 17 may be made of metal, while the remaining components may be made of a proper material other than metal.

Further, it may be configured so that the stage 20 is heated by radiating light from the ultraviolet-ray radiating lamp 30, and heat generated in the stage 20 is transferred through the housing 10 to the ozone-removing filter 17.

Further, if the ultraviolet-ray radiation required for the implant 1 is achieved only by direct light from the ultraviolet-ray radiating lamp 30, the reflecting mirror 40 is unnecessary.

Further, all the cleaning processing devices according to the above embodiments are intended to generate ozone for cleaning a subject to be processed, namely, the implant 1, using ultraviolet rays from the ultraviolet-ray radiating lamp 30. Apart from the ultraviolet-ray radiating lamp 30, for example, an ozone generator using a discharge by a high frequency or high voltage may be installed, and the ozone generated from the ozone generator may come into contact with the implant 1.

Further, the subject to be processed by the cleaning processing device of the present invention may be other biological implants such as a femur implant, without being limited to a dental implant.

[Description of reference numerals of important parts]

| | |
|---|---|
| 1: implant | 1G: implant group |
| 2: threaded portion | 3: protrusion |
| 3a: upper surface | 3b: lower surface |
| 10: housing | 10a: front sidewall |
| 10b: rear sidewall | 10c, 10d: sidewall |
| 10e: upper wall | 10f: lower wall |
| 11: processing chamber | 12: ozone-removing chamber |
| 15: partition wall | 16: fan |
| 17: ozone-removing filter | 20: stage |
| 21: surface | 22: holding portion |
| 30: ultraviolet-ray radiating lamp | 31: light emitting pipe |
| 32: linear portion | 33: curved portion |
| 40: reflecting mirror | 41: planar minor |
| E: discharge hole | F1: inlet |
| F2: outlet | S: closed space |

What is claimed is:

1. A cleaning processing device for a biological implant intended to clean the biological implant by radiating ultraviolet rays to a surface of the biological implant and also causing ozone to come into contact with the surface thereof, the device comprising:
a housing, the housing including:
a processing chamber for cleaning the biological implant,
an ozone-removing chamber disposed above the processing chamber, the ozone-removing chamber for removing the ozone from the processing chamber, and
a partition wall for partitioning the processing chamber from the ozone-removing chamber, the partition wall being made of metal;
a plurality of ultraviolet-ray radiating lamps facing each other, with the biological implant positioned therebetween, disposed in the processing chamber of the housing to radiate the ultraviolet rays to the biological implant;
an ozone-removing filter portion disposed in the ozone-removing chamber; and
a fan for introducing atmospheric gas present in the processing chamber into the ozone-removing filter portion, the fan being driven in response to a completion of a cleaning process for the biological implant,
wherein heat caused by light from the ultraviolet-ray radiating lamps is transferred through the partition wall to the ozone-removing filter portion.

2. The cleaning processing device as set forth in claim 1, wherein
the ozone-removing filter portion is disposed on a flow path that is formed by the fan in the ozone-removing chamber, and
the atmospheric gas present in the processing chamber is circulated through the ozone-emoving chamber, by driving the fan.

3. The cleaning processing device as set forth in claim 1, wherein the housing is made of metal, and the heat caused by the light from the ultraviolet-ray radiating lamps is transferred through the housing made of metal to the ozone-removing filter portion.

4. The cleaning processing device as set forth in claim 2, wherein the housing is made of metal, and the heat caused by the light from the ultraviolet-ray radiating lamps is transferred through the housing made of metal to the ozone-removing filter portion.

5. The cleaning processing device as set forth in any one of claims 1, 2, 3, and 4, wherein the ozone-removing filter portion includes a plurality of ozone-removing filters, which are provided on the flow path formed by the fan in such a way as to be located on both an upstream side and a downstream side of the fan, with a closed space defined between the ozone-removing filters.

6. The cleaning processing device as set forth in any one of claims 1, 2, 3, and 4, wherein a reflecting mirror made of metal is disposed in the processing chamber to reflect the light from the ultraviolet-ray radiating lamps, and the heat caused by the light from the ultraviolet-ray radiating lamps is transferred through the reflecting mirror to the ozone-removing filter portion.

7. The cleaning processing device as set forth in claim 6, wherein the ozone-removing filter portion includes a plurality of ozone-removing filters, which are provided on the flow path formed by the fan in such a way as to be located on both an upstream side and a downstream side of the fan, with a closed space defined between the ozone-removing filters.

* * * * *